US011731128B2

(12) United States Patent
Doong et al.

(10) Patent No.: US 11,731,128 B2
(45) Date of Patent: Aug. 22, 2023

(54) MICROCHANNEL CHIP, MICROCHANNEL STRUCTURE AND DETECTING METHOD USING THE SAME

(71) Applicant: LifeCode Biotech, Tapei (TW)

(72) Inventors: Joe-Yuan Doong, Chiayi (TW); Sung-Chi Tsai, Chiayi (TW)

(73) Assignee: LIFECODE BIOTECH, Taipei (TW)

( * ) Notice: Subject to any disclaimer, the term of this patent is extended or adjusted under 35 U.S.C. 154(b) by 641 days.

(21) Appl. No.: 16/823,595

(22) Filed: Mar. 19, 2020

(65) Prior Publication Data
US 2021/0291174 A1 Sep. 23, 2021

(51) Int. Cl.
*C12N 15/10* (2006.01)
*B01L 3/00* (2006.01)
(Continued)

(52) U.S. Cl.
CPC ..... *B01L 3/502715* (2013.01); *B01L 3/50273* (2013.01); *B01L 3/502761* (2013.01);
(Continued)

(58) Field of Classification Search
CPC ........... B01L 3/502715; B01L 3/50273; B01L 3/502761; B01L 2200/0647; B01L 2300/06; B01L 2300/0819; B01L 2300/0832; B01L 2300/0848; B01L 2300/0858; B01L 2300/0883; B01L 2300/12; B01L 2400/08; B01L 2200/0668; B01L 3/502746; G01N 33/5091; G01N 33/54366; G01N 33/57492
See application file for complete search history.

(56) References Cited

U.S. PATENT DOCUMENTS

2018/0250671 A1* 9/2018 De Lange ............. B01L 3/5027

FOREIGN PATENT DOCUMENTS

TW M581591 8/2019
TW M 581892 8/2019
(Continued)

OTHER PUBLICATIONS

Nagrath et al. "Isolation of rare circulating tumour cells in cancer patients by microchip technology" Nature. Dec. 20, 2007; 450(7173): 1235-1239.

*Primary Examiner* — Jennifer Wecker
*Assistant Examiner* — Oyeleye Alexander Alabi
(74) *Attorney, Agent, or Firm* — Allen, Dyer, Doppelt + Gilchrist, PA

(57) ABSTRACT

The present invention provides a microchannel structure loaded with a bead having a particle size for detecting whether a biological substance exists in a sample. The microchannel structure includes a structure body for passing a sample through the microchannel structure to have a test or a treatment. The structure body includes a sample entrance having a first aperture to allow the sample passing therethrough, a resistance-increasing section connected with the sample entrance, and having a second aperture being smaller than the first aperture, a detecting section connecting with the resistance-increasing section, and a bead mooring structure coupled to the second end for mooring the bead in the detecting section. The present invention can be used to capture rare cells in a biological system, such as human blood.

10 Claims, 14 Drawing Sheets
(3 of 14 Drawing Sheet(s) Filed in Color)

(51) Int. Cl.
*G01N 21/3504* (2014.01)
*G01N 33/00* (2006.01)
*G01N 33/574* (2006.01)
*G01N 21/64* (2006.01)
*A61K 45/06* (2006.01)
*G01N 21/35* (2014.01)
*G01N 33/50* (2006.01)

(52) U.S. Cl.
CPC .. *G01N 33/5091* (2013.01); *B01L 2200/0647* (2013.01); *B01L 2300/06* (2013.01); *B01L 2300/0819* (2013.01); *B01L 2300/0832* (2013.01); *B01L 2300/0848* (2013.01); *B01L 2300/0858* (2013.01); *B01L 2300/0883* (2013.01); *B01L 2300/12* (2013.01); *B01L 2400/08* (2013.01)

(56) References Cited

FOREIGN PATENT DOCUMENTS

| | | |
|---|---|---|
| TW | M583455 | 9/2019 |
| TW | M 583456 | 9/2019 |
| TW | M583855 | 9/2019 |
| TW | M590971 | 2/2020 |

\* cited by examiner

MICROCHANNEL CHIP, MICROCHANNEL STRUCTURE AND DETECTING METHOD USING THE SAME

FIELD OF THE INVENTION

The present invention is related to a microchannel chip, a microchannel structure and detecting method that can increase the catching rate for a biological substance. Particularly, the present invention is related to a microchannel chip, a microchannel structure and detecting method that can rapidly catch circulating tumor cells (CTC) in blood.

BACKGROUND OF THE INVENTION

The high mortality rate caused by cancer has been a serious problem in the health care field for a long time. Studies have found that tumors are mostly an organ-constrained disease, but the tumor is always transmitted to a distant organ through the bloodstream, forming a metastasis. Such distant metastasis is the main cause of death in tumor patients. Cells that fall off the primary site of the tumor and enter the blood circulation system are called circulating tumor cells (CTCs). CTCs are considered to be a necessary prerequisite for the occurrence of the distal tumor metastasis. The accurate counting and molecular markers of CTCs are important indicators for the prognosis judgment and evaluation of the curative effect on tumor patients.

The number of CTCs will change dynamically, depending on the changes of the tumor and the response to the treatment. Therefore, CTCs can be used for early diagnosis in vitro, rapid evaluation of drugs, and personalized treatment. However, in cancer patients, CTCs are relatively rare. It's about one CTC per $10^9$ blood cells, which means CTCs are difficult to detect and isolate technically. Therefore, a centralized collection method must be used to effectively isolate and detect CTCs.

One example of the centralized collection method at present is the use of highly expressed cell surface biomarkers, such as epithelial cell adhesion molecules (EpCAM) which are well-known to be specific and sensitive to CTC. Nagrath et al. (Nature 2007, 450: 1235-9) developed an anti-EpCAM antibody-coated microfluidic chip for CTC detection and collection. However, the drawback of using the anti-EpCAM antibody-coated microfluidic chip is the low capture rate and hence the low detection rate of CTCs. This may be attributed to a bad design causing inefficient binding with CTCs or non-specific binding of blood cells to anti-EpCAM antibodies.

Despite the advances of the technology for the detection and isolation of CTCs, more specific and effective binding assays are needed to detect, purify, and release CTCs and other biological substances for further characterization and CTC cell culture.

It is therefore the Applicant's attempt to deal with the above situation encountered in the prior art.

SUMMARY OF THE INVENTION

A novel microchannel system is provided in the present invention, including a microchannel chip with beads loaded in the microchannel chip, and the beads are used to catch and isolate circulating tumor cells (CTCs) from blood. The principle is to utilize specific interaction between the surface antigens of circulating tumor cells and the antibodies implanted on the surface of the beads. Because the bead has the largest contact area (per unit volume) to interact with the CTCs, and because the design of the microchannel structure may increase fluid resistance, causing a turbulent flow effect which may promote the rotating or rolling of CTCs, the probability to catch CTCs onto the beads can be significantly increased. Based on a unique design of the microchannel structure in the present invention, non-specific binding of the blood cells with anti-EpCAM antibodies can be minimized.

In accordance with another aspect of the present disclosure, a microchannel chip loaded with a bead having a particle size is disclosed. The microchannel chip includes: a substrate; a body having a first surface, and a second surface covering the substrate; and a patterned structure formed on the second surface to form a microchannel between the body and the substrate, wherein the microchannel includes: a sample entrance extended from the first surface to the second surface, wherein the sample entrance has a diameter to pass a sample therethrough; an expanding section communicating with the sample entrance, wherein the expanding section has a first width; a resistance-increasing section communicating with the expanding section, wherein the resistance-increasing section has a second width; a detecting section communicating with the resistance-increasing section, wherein the bead is configured in the detecting section; and a slow flow section communicating with the detecting section, and having a first depth, wherein the particle size is larger than the first depth to prevent the bead from entering the slow flow section, the second width is smaller than either of the first width and the diameter, and the bead is moored in the detecting section.

In accordance with one more aspect of the present disclosure, a microchannel structure loaded with a bead having a particle size is disclosed. The microchannel structure includes: a structure body for passing a sample through the microchannel structure to have a test or a treatment, wherein the structure body includes: a sample entrance having a first aperture to allow the sample passing therethrough; a resistance-increasing section connected with the sample entrance, and having a second aperture being smaller than the first aperture; a detecting section having a first end and a second end for testing or treating the sample, wherein the first end connects with the resistance-increasing section; and a bead mooring structure coupled to the second end for mooring the bead in the detecting section.

In accordance with one more aspect of the present disclosure, a method for detecting whether a biological substance exists in a sample using a microchannel structure is provided. The method includes: providing a microchannel structure including a plurality of beads moored therein, wherein a plurality of catchers are coated on a surface of each of the plurality of beads, and the plurality of catchers catch the biological substance in the sample; obtaining the sample; and causing the sample to flow through the microchannel structure so as to confirm whether the biological substance exists in the sample.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Other objectives, advantages and efficacies of the present invention will be described in detail below taken from the preferred embodiments with reference to the accompanying drawings.

FIGS. 11(A)~11(C) show an image diagram of the isolation result of a blood specimen flowing through the microchannel chip of the present invention, wherein FIG. 11(A) shows CTCs (the green fluorescence) were caught by the beads in the microchannel chip, FIG. 11(B) shows white blood cells (the red fluorescence) were erroneously caught by the beads in the microchannel chip, and FIG. 11(C) shows the sites of all cells caught by the beads by combining FIGS. 11(A) and 11(B).

DETAILED DESCRIPTION OF THE PREFERRED EMBODIMENTS

Figure 1A:
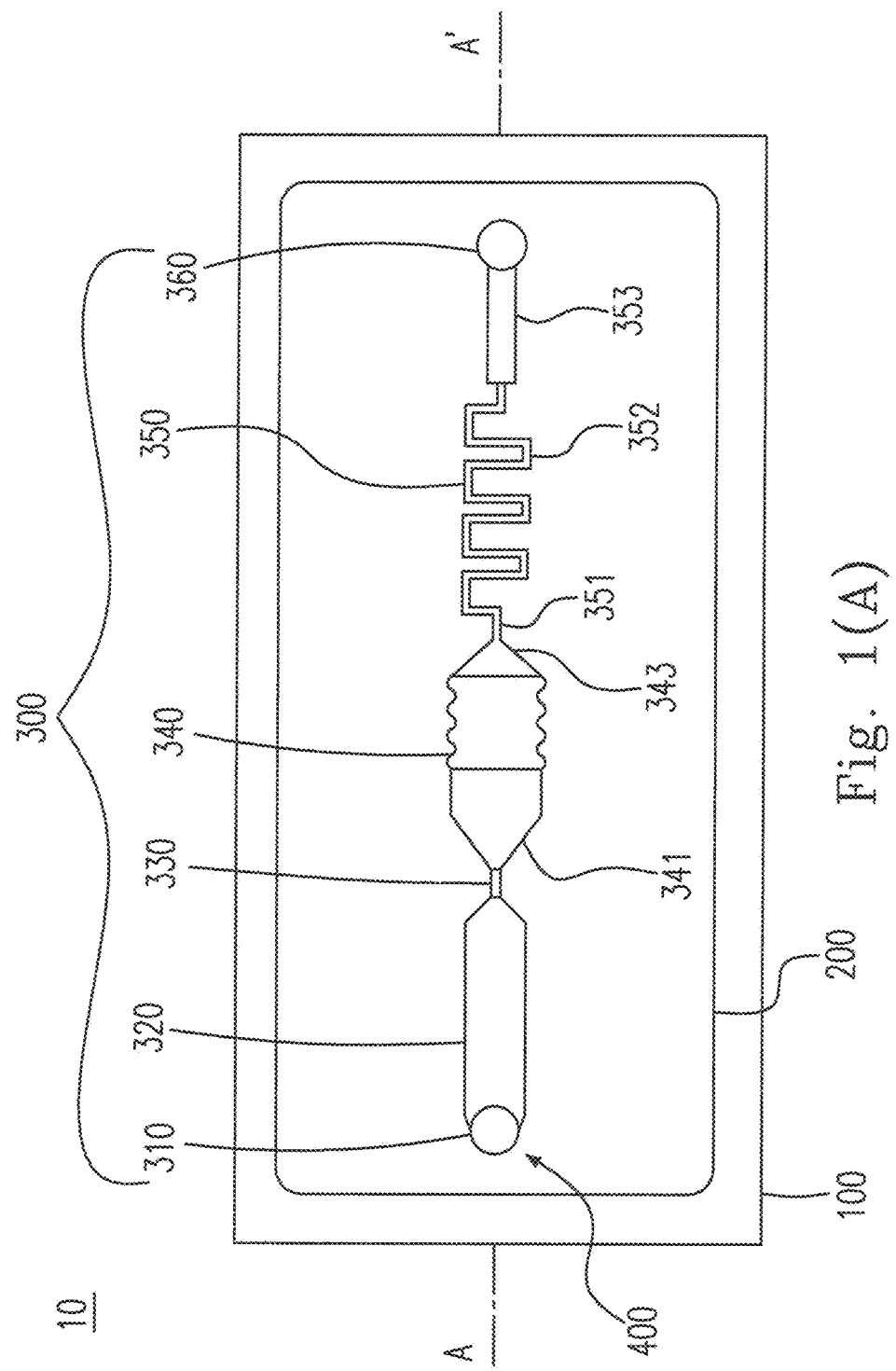
FIG. 1(A) shows a top schematic diagram of a microchannel chip of the present invention.

The present invention will now be described more specifically with reference to the following embodiments. It is to be noted that the following descriptions of preferred embodiments of this invention are presented herein for purpose of illustration and description only; they are not intended to be exhaustive or to be limited to the precise form disclosed. In the preferred embodiments, the same reference numeral represents the same element in each embodiment.

The microchannel chip of the present invention loads beads, especially large beads. The particle size of the beads is 100~200 μm. There are substances coated on the beads, which is: (1) releasable components that can release or remove non-specific blood cells and other blood components, such as protein; (2) bioactive components (regarding as a catcher) that can catch biological substances; and (3) connection molecules that connect to the releasable components and bioactive components. When the sample flows through the beads, the bead can catch the biological substances which can react with the bioactive components on the surface of the beads in the sample, and can release the caught biological substance for a further research and detection. The material of the bead can be a transparent plastic or a transparent resin. The sample can be a body fluid or a bacterial solution. The body fluid includes blood, cerebrospinal fluid, various digestive fluids, semen, saliva, sweat, urine, vaginal fluid or solutions containing biological substances. The biological substance can be a circulating tumor cell (CTC), a circulating stem cell (CSC), a fetal cell, a bacteria, a virus, an epithelial cell, an endothelial cell or other biological substances. The circulating stem cell (CSC) includes cancer stem cell, liver stem cell and bone marrow stem cell. Therefore, the bioactive components coated on the surface of the bead will be different for different biological substances.

In an embodiment of the present invention, the sample is blood of the human body, the biological substance is circulating tumor cell (CTC), and the bioactive component is antibody of epithelial cell adhesion molecule (EpCAM).

In any embodiment of the present invention, each section of the microchannel includes an upper wall, a bottom wall, a left side wall and a right side wall. The aperture of each section of the microchannel includes a width and a depth, wherein the width represents a distance from the left side wall to the right side wall, and the depth represents a distance from the upper wall to the bottom wall.

Please refer to FIGS. 1(A), 1(B), 2(A), 2(B), 3(A), 3(B) and 3(C), which are top schematic diagrams and sectional schematic diagrams of the microchannel chip of the present invention. The microchannel chip 10 of the present invention loads a bead 40 and includes a substrate 100, a body 200, and a patterned structure 400. The bead 40 has a particle size. The body 200 has a first surface 210 and a second surface 220 opposite to the first surface 210, and the second surface 220 covers the substrate 100. The patterned structure 400 is formed on the second surface 220 of the body 200 to form a microchannel 300 between the body 200 and the substrate 100.

The microchannel 300, from the entrance to the exit, sequentially includes a sample entrance 310, an expanding section 320, a resistance-increasing section 330, a detecting section 340, a slow flow section 350 and a sample exit 360.

The sample entrance 310 of the present invention extends from the first surface 210 to the second surface 220 in the substrate 100 to pass a sample therethrough. The sample entrance 310 can be a circular or a polygonal aperture, preferably the circular aperture. The sample entrance 310 has a diameter between 0.8~1.2 mm, which lets an injector having 18~21G (about 0.7~0.9 mm) needle be inserted therein.

The expanding section 320 has a first end 321 and a second end 322. The first end 321 communicates with the sample entrance 310, and the second end 322 communicates with the resistance-increasing section 330. The expanding section 320 has an aperture which can be a circle or a polygon, preferably a square. Because there may occur a rapid flow at the front when plenty of the sample enters from the sample entrance 310, a width of the expanding section 320 is larger than the diameter of the sample entrance 310 for cushioning the rapid flow of the sample, to increase a unit flow (volume passed per second) of the expanding section 320, and prevent the sample from leaking due to excessive hydraulic pressure. The width of the expanding section 320 of the present invention sets between 0.8~1.5 mm, and a depth of the expanding section 320 is 1 mm.

An end of the resistance-increasing section 330 of the present invention communicates with the second end 322 of the expanding section 320, and the other end of the resistance-increasing section 330 communicates with the detecting section 340. The resistance-increasing section 330 has an aperture which can be a circle or a polygon, preferably a square. The width of the resistance-increasing section 330 is smaller than the width of the expanding section 320 and the diameter of the sample entrance 310, and larger than the particle size of the bead 40. Therefore, the resistance-increasing section 330 can provide a passage to pass the bead 40 therethrough and to enhance a fluid resistance simultaneously, which has the function of preventing the sample from bursting, limiting the flow of the sample and preventing the sample from flowing back due to the removal of the needle from the sample entrance 210. The width of the resistance-increasing section 330 of the present invention is 250 µm, and the depth of the resistance-increasing section 330 is 1 mm. Because the width of the expanding section 320 is larger than that of the resistance-increasing section 330, the width of the second end 322 of the expanding section 320 can be gradually narrowed to the width of the resistance-increasing section 330. That is, the width of the second end 322 of the expanding section 320 is gradually narrowed from 0.8~1.5 mm to 250 µm.

Figure 3A:
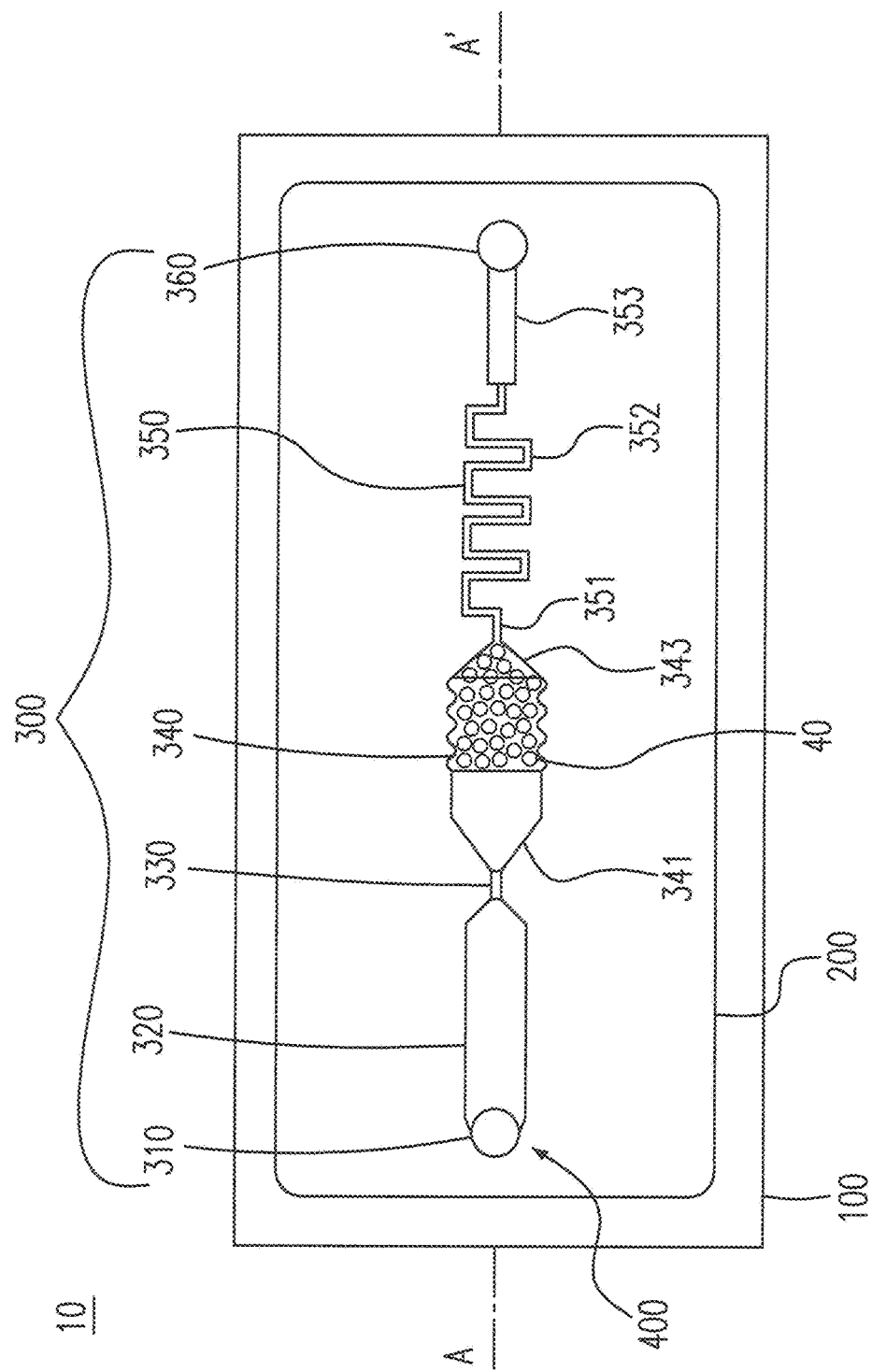
FIG. 3(A) shows a schematic diagram of the bead loaded in the detecting section of the microchannel chip of the present invention.
Figure 3B:
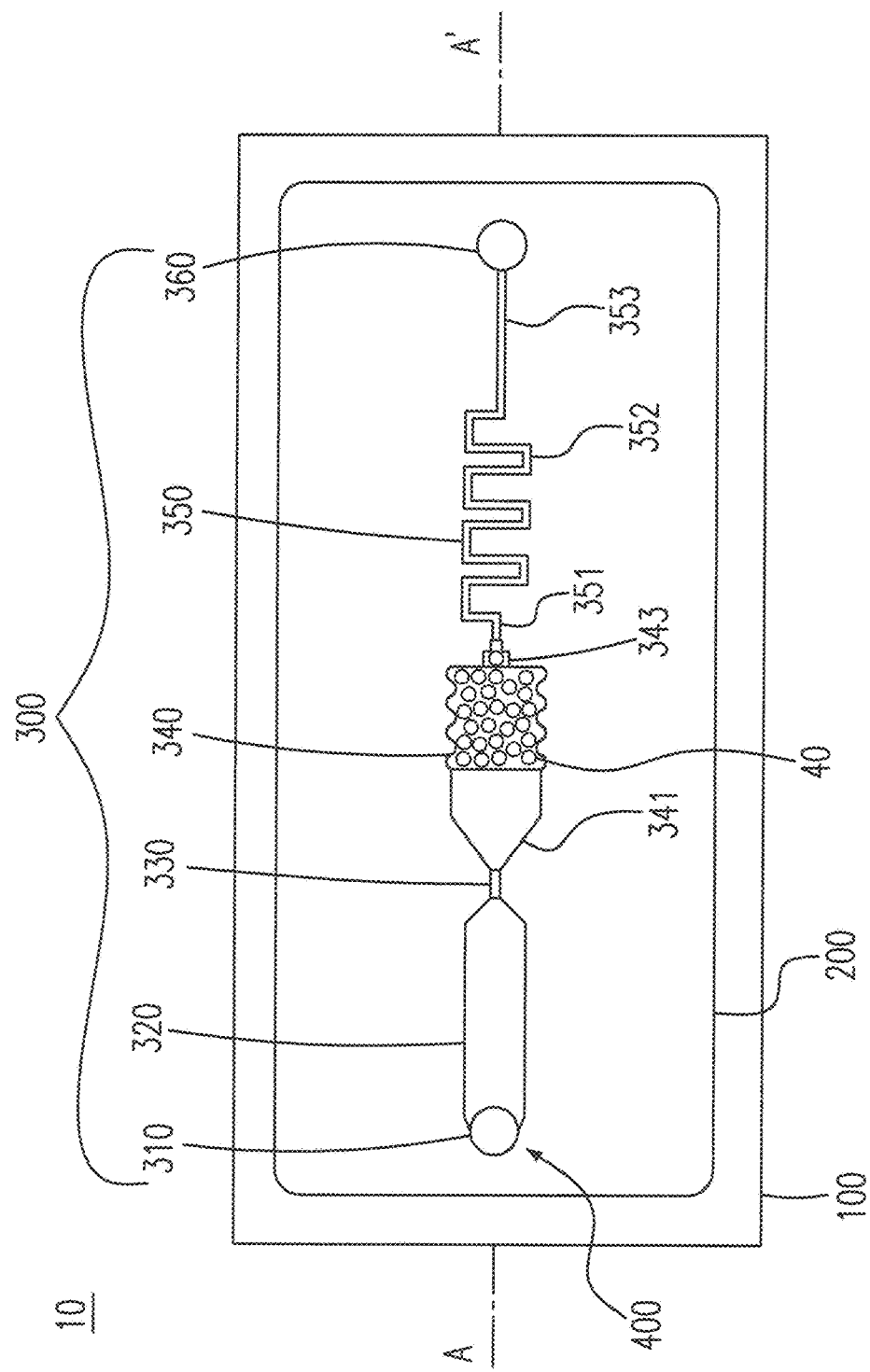
FIG. 3(B) shows a schematic diagram of the bead loaded in the detecting section of another embodiment of the microchannel chip of the present invention.
Figure 3C:
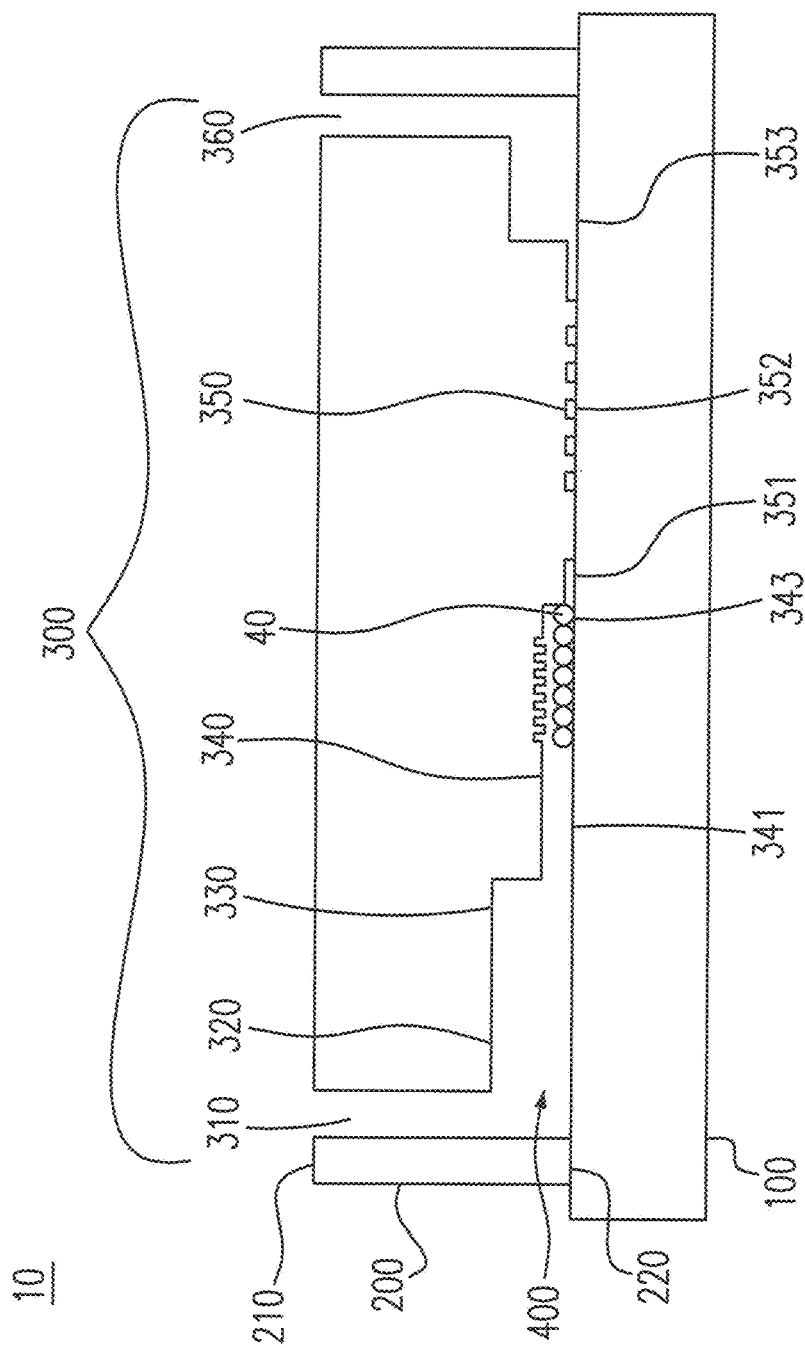
FIG. 3(C) shows a sectional schematic diagram of the microchannel chip with bead of the present invention
Figure 4:
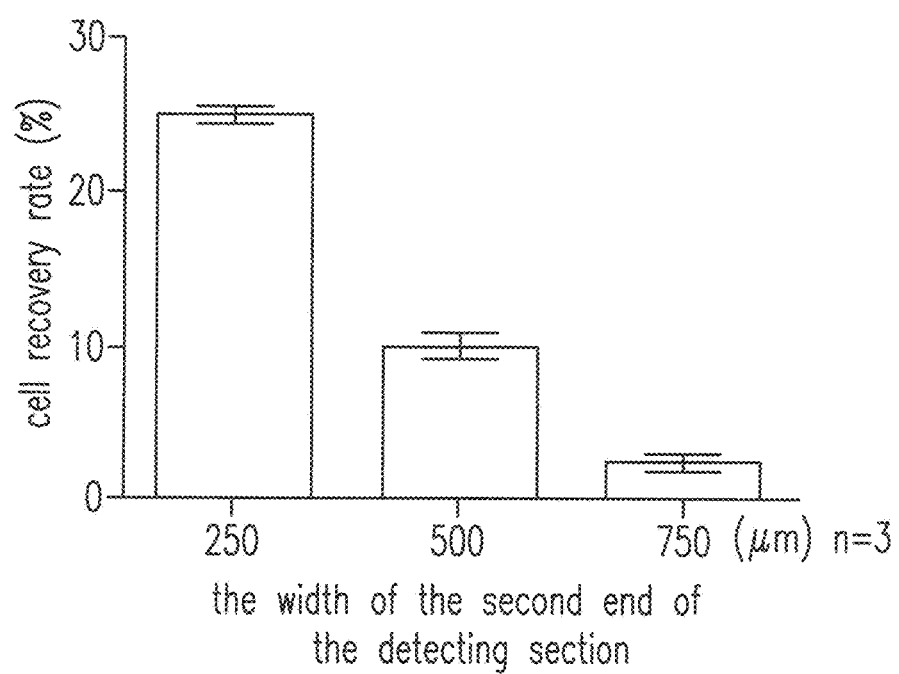
FIG. 4 shows an influence result of the cell recovery rate by different width of the second end of the detecting section.

The detecting section 340 of the present invention includes a first end 341, a main detecting section 342 and a second end 343, wherein the first end 341 communicates with the resistance-increasing section 330, the second end 343 communicates with the slow flow section 350, and the main detecting section 342 sets between the first end 341 and the second end 343. The bead 40 catching the biological substance is configured in the main detecting section 342, as shown in FIGS. 3(A) and 3(B). The detecting section 340 has an aperture which can be a circle or a polygon, preferably a square. In an embodiment of the present invention, the aperture of the detecting section 340 is square. The depth of the detecting section 340 is limited for the bead not to pile but in a single layer in the detecting section 340, as shown in FIG. 3(C). Therefore, the depth of the detecting section 340 is the particle size of the bead 40 plus 20~50 µm, and hence, the depth of the detecting section 340 sets between 120 µm~250 µm. The width of the first end 341 and the main detecting section 342 of the detecting section 340 is enough for the bead 40 passing through. Therefore, the width of the first end 341 and the main detecting section 342 of the detecting section 340 set between 250 µm~1.5 mm. The width of the first end 341 of the detecting section 340 can be the same as that of the resistance-increasing section 330, or the width of the first end 341 of the detecting section 340 is gradually increased from that of the resistance-increasing section 330 to that of the first end 341. The main detecting section 342 can accommodate about 20~30 beads. The width of the second end 343 of the detecting section 340 affects the arrangement of the bead 40 at the second end 343, and the arrangement of the bead 40 affects the fluidic direction of the sample. According to the experiment result of FIG. 4, when the particle size of the bead is 200 µm, and the width of the second end 343 of the detecting section 340 is 250 µm (i.e. only accommodates 1 bead 40 at the second end 343), the cell recovery rate is the best, and as the width of the second end 343 increases, the cell recovery rate decreases. Therefore, the width of the second end 343 of the detecting section 340 can be a width only for accommodating 1 bead. The width of the second end 343 of the detecting section 340 sets between 150 µm~250 µm. Because the width of the main detecting section is larger than that of the second end 342, the width of the second end 343 can be gradually (as shown in FIG. 1(A)) or stepwise (as shown in FIG. 1(A)) narrowed from the width of the main detecting section 342 to the width of the second end 343.

Figure 5A:
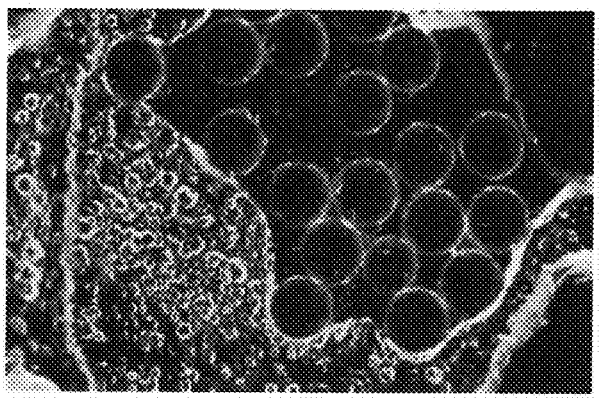
FIGS. 5(A)-5(B) show image diagrams of the result when there is no resistance-increasing section in the microchannel chip in the present invention.
Figure 5B:
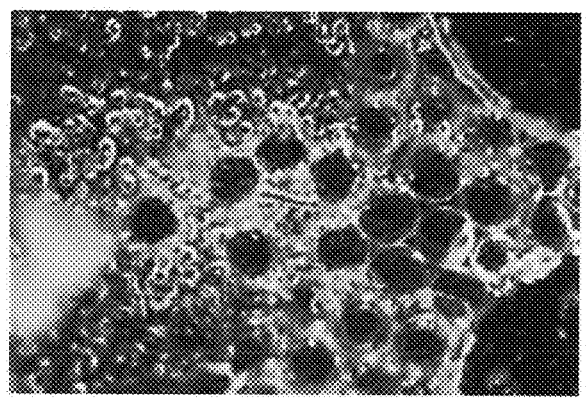
Figure 5C:
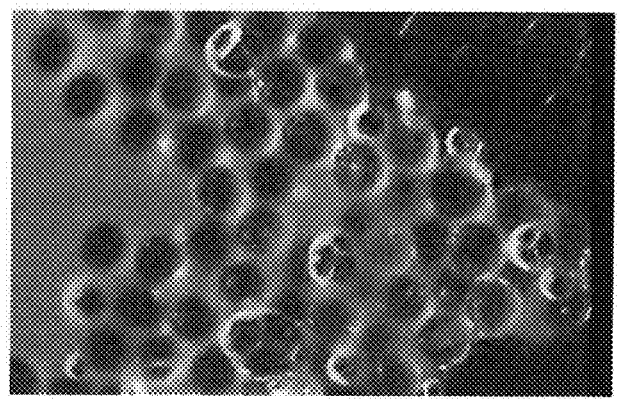
FIG. 5(C) shows an image diagram of the result of the microchannel chip with the resistance-increasing section in the present invention.

The resistance-increasing section 330 can enhance the fluid resistance to prevent the sample from bursting to the detecting section 340, control the sample flowing into the detecting section 340, and prevent the sample from the detecting section 340 flowing back to the expanding section 320 due to the removal of the needle from the sample entrance 210. Please refer to FIGS. 5(A) and 5(B), if there is no resistance-increasing section 330 at the front end of the microchannel chip 10, the arrangement of the bead 40 in the detecting section 340 will be disordered, lots of bubbles will be produced due to the bursting of the sample, and the bead will not be able to catch the biological substance. Please refer to FIG. 5(C), when the resistance-increasing section 330 is configured at the front end of the microchannel chip 10, there is no bubble produced in the detecting section 340 and the bead 40 will not be moved back, so as to catch the biological substance.

For mooring the bead 40 in the main detecting section 342 and to ensure it does not move with the fluid flowing, the microchannel structure 300 includes a bead mooring structure 344. The bead mooring structure is coupled to the second end 343 of the detecting section 340. The aperture of the bead mooring structure 344 is smaller than the particle size of the bead 40, so that the bead cannot enter the slow flow section 350 through the bead mooring structure, and so as to moor the bead 40 in the main detecting section 342. In addition, the resistance-increasing section 330 has the function of preventing the sample from the detecting section 340 from flowing back to the expanding section 320, and the bead 40 will not move with the needle insertion. Therefore, the bead 40 can stably stay in the main detecting section 342, so as to conveniently observe the state of the biological substance adsorbed by the bead 40. The bead mooring structure 344 of the present invention can be the second end 343 of the detecting section 340. Hence, in this condition, the aperture of the second end 343 of the detecting section 340 is smaller than the particle size of the bead 40, as shown in FIG. 3(B).

Figure 1B:
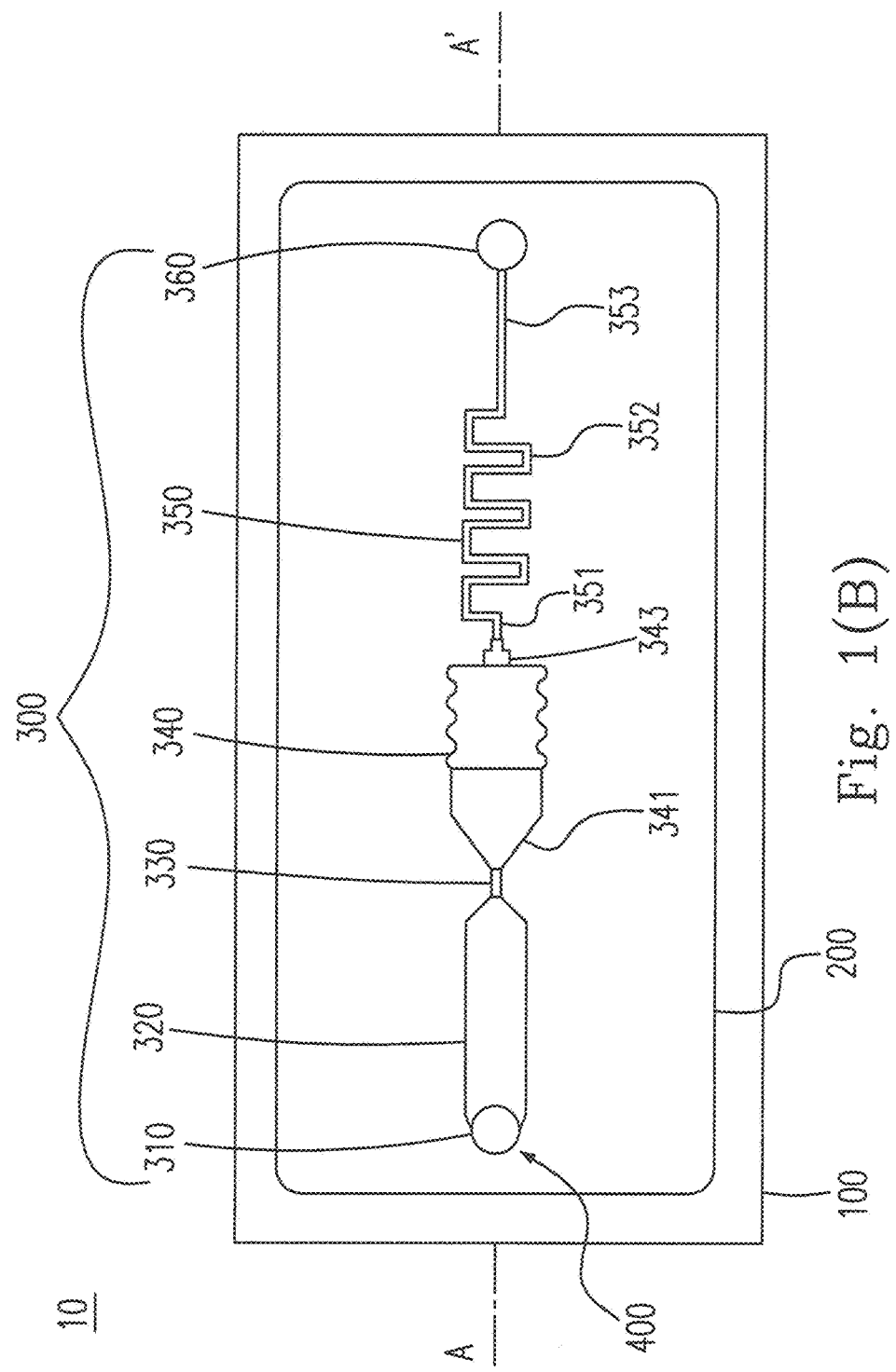
FIG. 1(B) shows a top schematic diagram of another embodiment of the microchannel chip of the present invention.
Figure 2A:
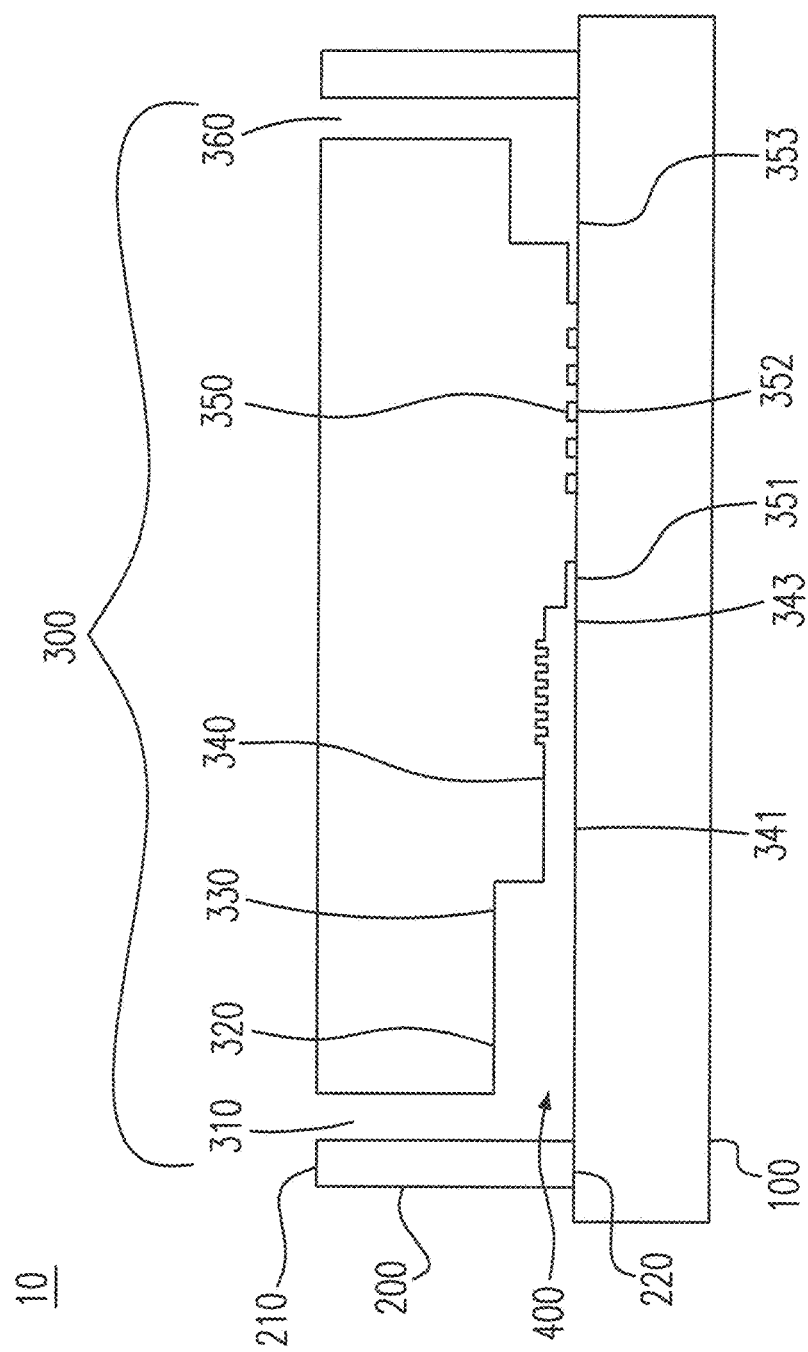
FIG. 2(A) shows a sectional schematic diagram of a cut view of the microchannel chip along the section line A-A' in FIG. 1(A).
Figure 2B:
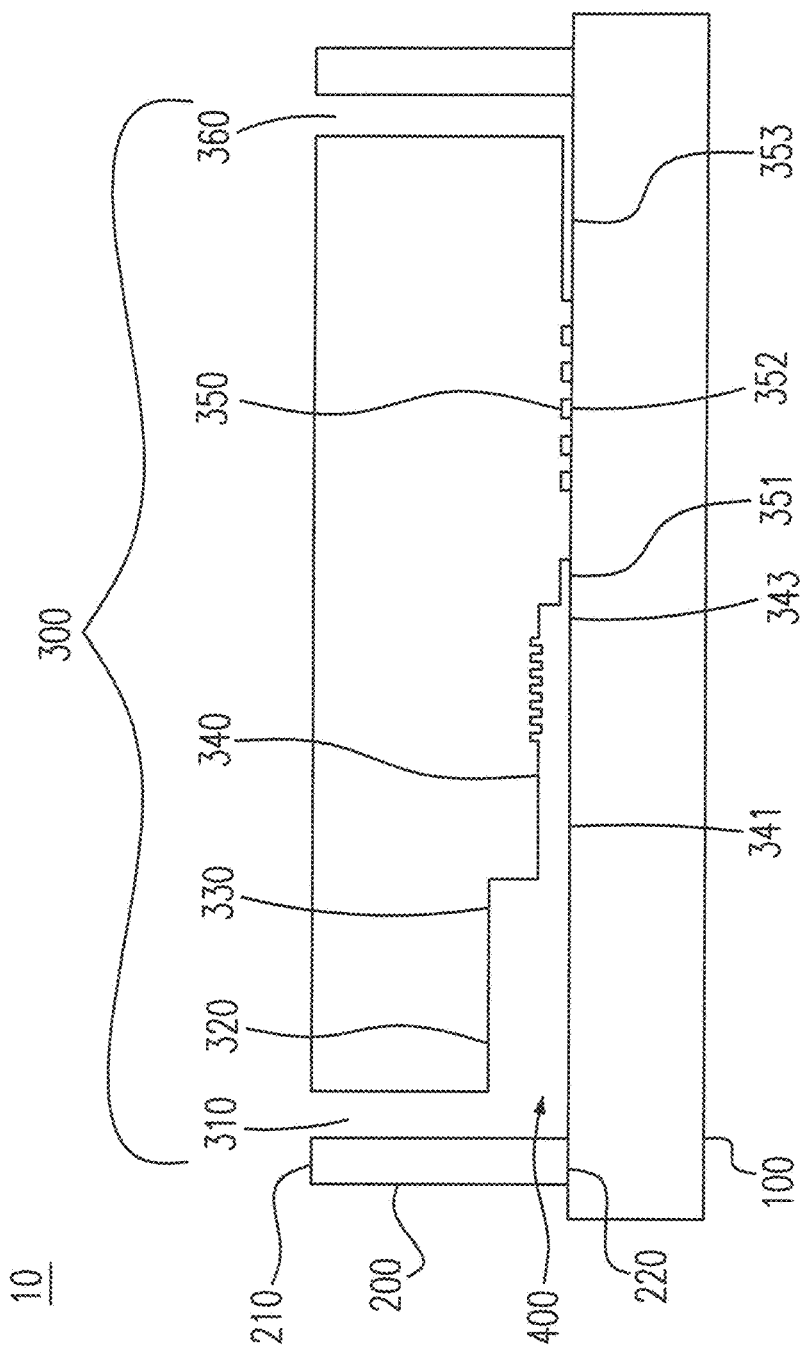
FIG. 2(B) shows a sectional schematic diagram of a cut view of another embodiment of the microchannel chip along the section line A-A' in FIG. 1(B).
Figure 6:
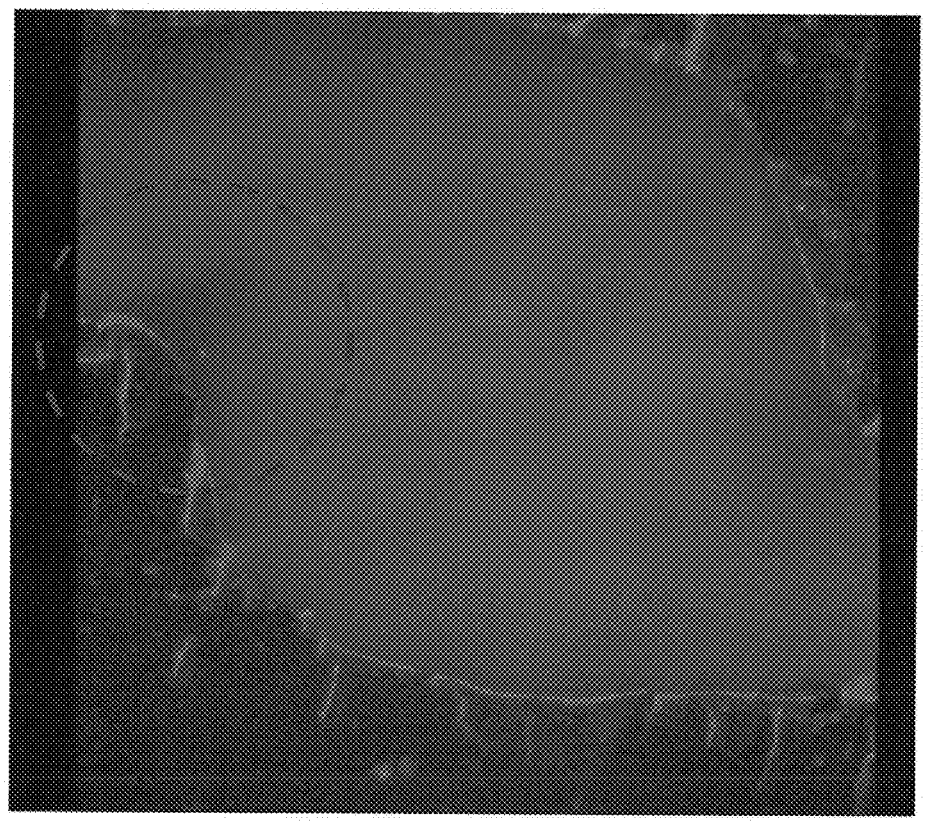
FIG. 6 shows an image diagram of a turbulent flow effect resulting from the uneven structure.
Figure 7:
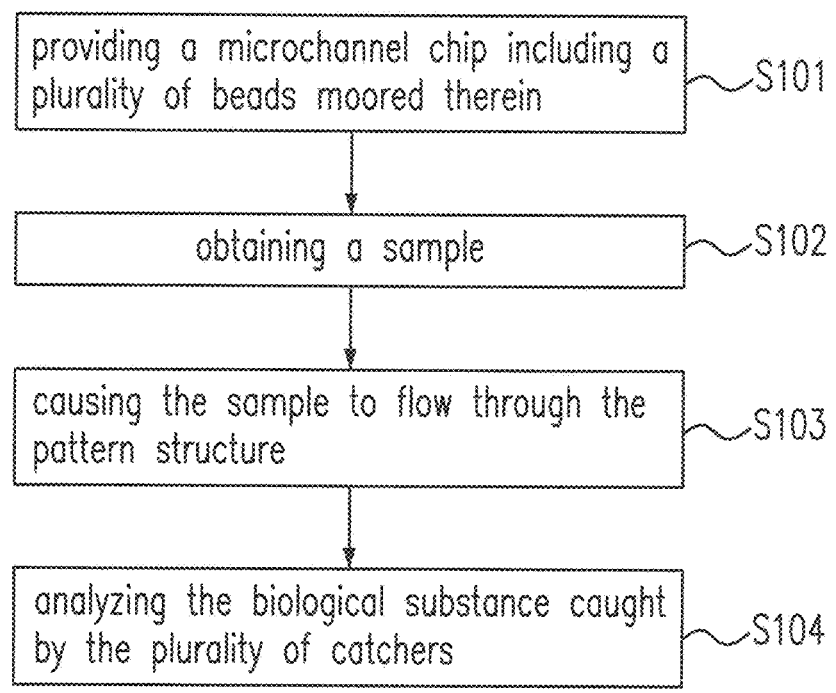
FIG. 7 shows a flowchart of a detecting method using the microchannel chip having the pattern structure of the present invention.

In the main detecting section 342, the main detecting section 342 includes a peripheral wall, and at least a portion of the peripheral wall has an uneven structure. Specifically, when the aperture of the main detecting section is a circle, at least the portion of the peripheral wall is the uneven structure, and when the aperture of the main detecting section is a polygon, the peripheral wall includes two side walls and an upper wall, and at least one wall of the peripheral wall is the uneven structure. The uneven structure can be a comb structure, a wave structure, a sawtooth structure, a semi-circular protrusion structure, or a combination thereof. For example, the uneven structure of the two side walls of the main detecting section 342 is the wave structure as shown in FIGS. 1(A) and 1(B), and the uneven structure of the upper wall of the main detecting section 342 is the comb structure as shown in FIGS. 2(A) and 2(B). The uneven structure of the main detecting section 342 can confront a flow of the sample when the sample is flowing, and disorder an original flow direction of the sample, so as to increase a turbulence level of the flow to increase a contact chance of the sample with the bead 40. Please refer to FIG. 6, which shows an image diagram of a turbulent flow effect resulting from the uneven structure. When the sample hits the wave structure of the side walls of the main detecting section 342, the turbulence effect having 10 μm oscillation amplitude is occurring, as shown as the red circle in FIG. 6. The biological substance will roll or turn because of the oscillation by the wave structure, so as to increase the contact chance of the biological substance with the bead 40. The size of the uneven structure can be the same or be different. The width or the radius of the uneven structure can be 30~50 μm. In an embodiment of the present invention, the upper wall of the main detecting section 342 is the comb structure having 50 μm width, and the side walls of the main detecting section 342 is the wave structure having 30 μm radius.

The slow flow section 350 of the present invention includes a first end 351, a main slow flow section 352 and a second end 353, wherein the first end 351 of the slow flow section 350 communicates with the second end 343 of the detecting section 340, the second end 353 of the slow flow section 350 communicates with the sample exit 360, and the main slow flow section 352 sets between the first end 351 and the second end 353. The main slow flow section 352 can be a linear structure (not shown in figure) or a labyrinth structure, as shown in FIGS. 1(A), 1(B), 3(A) and 3(B), preferably the labyrinth structure. The aperture of the slow flow section 350 is circular or polygonal, preferably a square. In an embodiment of the present invention, the aperture of the slow flow section 350 is square. The width of the first end 351 and the main slow flow section 352 of the slow flow section 350 can be equal to or small than that of the second end 343 of the detecting section 340, and the depth of the first end 351 and the main slow flow section 352 of the slow flow section 350 is smaller than that of the detecting section 340. For speeding up the sample which has passed through the main slow flow section 352 leaving the microchannel structure 300, the aperture of the second end 353 of the slow flow section 350 is larger than that of the main slow flow section 352, as shown in FIGS. 1(A), 2(A) and 3(A). In another embodiment, the aperture of the second end 353 of the slow flow section 350 also can be the same as that of the main slow flow section 352 as shown in FIGS. 1(B), 2(B) and 3(B). The width of the slow flow section 350 sets between 150~250 μm, and the depth of the first end 351 and the main slow flow section 352 of the slow flow section 350 sets between 50~100 μm.

In another embodiment of the present invention, for preventing the bead 40 from entering the slow flow section 350 and mooring the bead 40 in the main detecting section 342, the bead mooring structure 344 can be the first end 351 of the slow flow section 350. Therefore, in this condition, the depth of the first end 351 of the slow flow section 350 is smaller than the particle size of the bead 40 (as shown in FIG. 3(C)). Accordingly, the bead mooring structure 344 coupling to the second end 343 of the detecting section 340 indicates that the bead mooring structure 344 is the second end 343 of the detecting section 340, or connects to the second end 343 of the detecting section 340.

For stabilizing the flow rate of the sample in the microchannel chip 10, there are some specific characteristics for the slow flow section 350. The characteristics includes: (1) the depth of the slow flow section 350 is smaller than that of the second end 343 of the detecting section 340, as shown in FIGS. 2(A) and 2(B); (2) the depth of the second end 343 of the detecting section 340 is 1.2~50 times larger than that of the slow flow section 350; and (3) the structure of the main slow flow section 352 is the labyrinth structure, as shown in FIGS. 1(A), 1(B), 3(A) and 3(B). These characteristics of the slow flow section 350 can increase the resistance of the fluid to slow the flow rate of the sample in the microchannel chip 10, which can make the flow rate of the sample keep consistent when passing through the main detecting section 342, so as to increase the probability of the bead 40 catching the biological substance.

The slower the flow rate of the sample, the higher adsorption efficiency of the bead 40. Table 1 shows the influence of the depth of the slow flow section 350 for the adsorption of the biological substance in the sample by the bead 40.

TABLE 1

|  | Width of slow flow section | Depth of slow flow section | Flow rate (μL/min) | Adsorption efficiency |
|---|---|---|---|---|
| Experiment1 | 250 μm | 100 μm | 20 | 10-20% |
| Experiment2 | 250 μm | 50 μm | 40 | 88% |

It can be seen in Table 1 that when the depth of the slow flow section 350 is 100 μm, the adsorption efficiency of the bead 40 is 10~20%, and when the depth of the slow flow section 350 is 50 μm, the adsorption efficiency of the bead 40 is 88%. Therefore, the smaller the depth of the slow flow section, the smaller a cross-section area of the slow flow section 350, and that will decrease the flow rate of the sample in the microchannel structure 300 and increase the adsorption efficiency of the bead 40.

An end of the sample exit 360 of the present invention communicates to the second end 353 of the slow flow section 350, and the other end of the sample exit 360 extends from the second surface 220 to the first surface 210 of the body. The sample passing through the microchannel 300 will flow to a waste liquid recovery area (figure not shown) through the sample exit 360. The sample exit 360 can be a circular or a polygonal aperture, preferably the circular aperture. The sample exit 360 has a diameter between 0.8~1.2 mm.

Table 2 shows the preferable embodiments of the particle size of the bead 40 and the aperture of each section of the microchannel structure 300

TABLE 2

|  |  | Embodiment 1 | Embodiment 2 |
|---|---|---|---|
| Particle size of bead |  | 100 μm | 200 μm |
| Diameter of sample entrance |  | 0.8 mm | 0.8 mm |
| expanding section | Width | 1 mm | 1 mm |
|  | Depth | 1 mm | 1 mm |
| resistance-increasing section | Width | 250 μm | 250 μm |
|  | Depth | 1 mm | 1 mm |
| First end of detecting section | Width | 1.5 mm | 1.5 mm |
|  | Depth | 120 μm | 220 μm |
| Main detecting section | Width | 1.5 mm | 1.5 mm |
|  | Depth | 120 μm | 220 μm |
| Second end of detecting section | Width | 150 μm | 250 μm |
|  | Depth | 120 μm | 220 μm |
| First end of slow flow section | Width | 150 μm | 250 μm |
|  | Depth | 50 μm | 100 μm |
| Main slow flow section | Width | 150 μm | 250 μm |
|  | Depth | 50 μm | 100 μm |
| Diameter of sample exit |  | 0.8 mm | 0.8 mm |

Please refer to FIGS. 1~4 and 7, the detecting method using the microchannel chip 10 having the pattern structure 400 of the present invention includes: providing the microchannel chip 10 including a plurality of beads 40 moored therein (Step S101); obtaining a sample (Step S102); causing the sample to flow through the pattern structure 400

(Step S103) so as to confirm whether the biological substance exists in the sample; and analyzing the biological substance caught by the plurality of catchers (Step S104). In Step S101, a plurality of catchers are coated on a surface of each of the plurality of beads 40, and the plurality of catchers catch the biological substance in the sample. In Step S102, the sample can be obtained from an organism, preferably blood from a human body. In Step S103, the sample flows through the sample entrance 310, the expanding section 320, the resistance-increasing section 330, the detecting section 340, the slow flow section 350 and the sample exit 360, wherein the catchers on the surface of the bead catch the biological substance in the sample at the detecting section 340, so that the biological substance isolated from the sample is located in the detecting section 340, and the treated sample (e.g. blood without the biological substance) flows to a waste liquid storage tank after flowing out of the sample exit 360. In Step S104, the biological substance located in the detecting section 340 can be observed directly using a microscope, and/or washed out by known techniques for further experiments.

The material of the substrate 100 in the present invention can be polymethylmethacrylate (PMMA), polyethylene terephthalate (PET), polycarbonate (PC), polydimethylsilicon (PDMS), silica gel, rubber, plastic or glass. The material of the 200 can be polymethylmethacrylate (PMMA), polyethylene terephthalate (PET), polycarbonate (PC), polydimethylsilicon (PDMS), silica gel, rubber or plastic. The material property between the substrate 100 and the body 200 should be considered when choosing the materials of the substrate 100 and the body 200. In an embodiment of the present invention, the material of the substrate 100 is glass, and the material of the body 200 is polydimethylsilicon.

Figure 8:
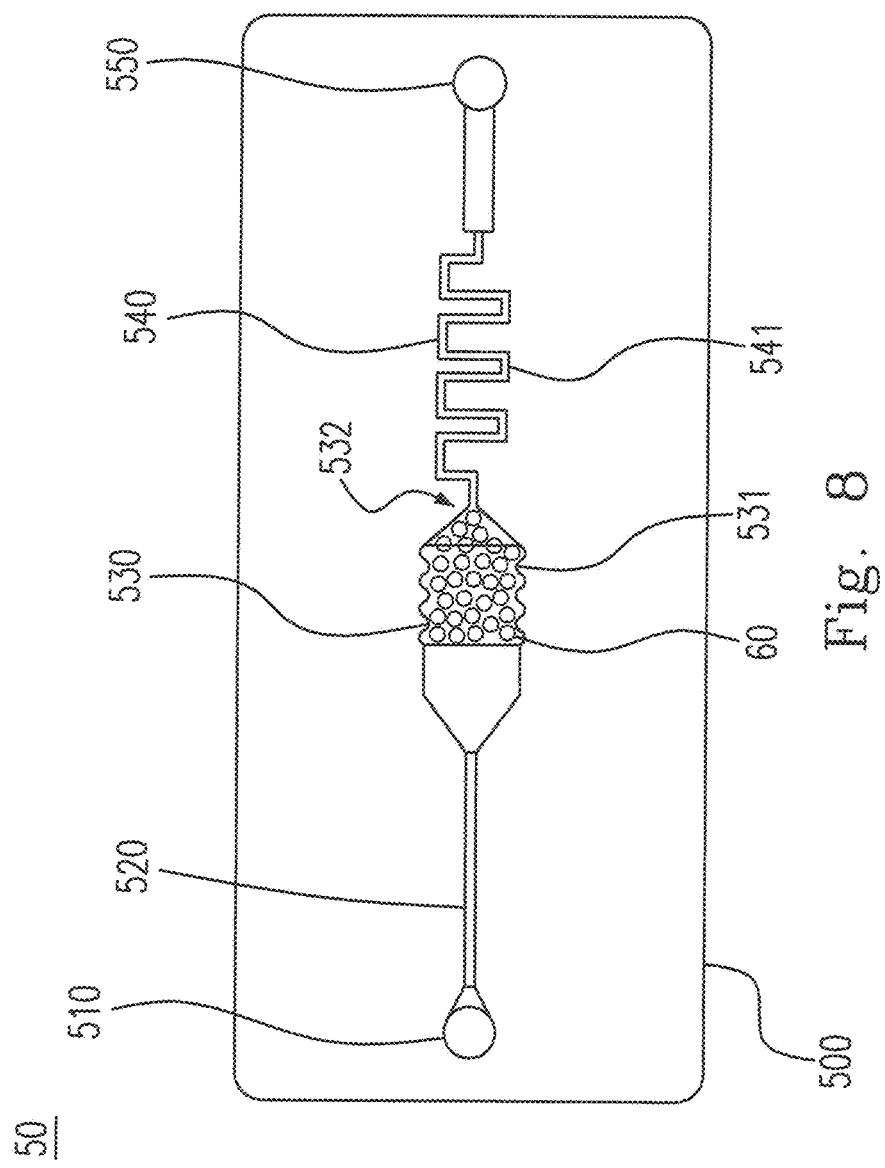
FIG. 8 shows a top schematic diagram of another embodiment of the microchannel structure of the present invention.

Another embodiment of a microchannel structure 50 is provided in the present invention, as shown in FIG. 8. The microchannel structure 50 is used for testing or treating a sample therein. The microchannel structure 50 loads a bead 60 and has a structure body 500. The structure body 500 from the entrance to the exit sequentially includes a sample entrance 510, a resistance-increasing section 520, a detecting section 530, a slow flow section 540 and a sample exit 550, wherein the bead 60 is set in the detecting section 530. The aperture of the resistance-increasing section 520 is smaller than that of the detecting section 530 to increase a fluid resistance of the sample in the microchannel structure 50. There is an uneven structure 531 at a peripheral part of the detecting section 530 to confront the flow direction of the sample. A bead mooring structure 532 is coupled between the detecting section 530 and the slow flow section 540 to moor the bead 60 in the detecting section 530. The slow flow section 540 has a main slow flow section 541 being a labyrinth structure to decrease the flow rate of the sample in the microchannel structure 50. When the sample enters from the sample entrance 510, it can directly enter the detecting section 530 through the resistance-increasing section 520 to have a test or a treatment by the bead 60, where the bead 60 catches the biological substance in the sample. The tested or treated sample enters the slow flow section 540, and finally flows out of the microchannel structure 50 from the sample exit 550.

The manufacturing method of the microchannel chip of the present invention includes: printing a master mold having a microchannel structure using a 3D printer, wherein the master mold is a light-cured resin washed by 95% alcohol; curing the master mold by UV light for 2 minutes; after washing by alcohol, baking the master mold for 10 minutes; pouring a food-grade material PDMS into the master mold; curing at 80 C for 50 minutes to obtain a body having the microchannel structure; and jointing the body with a glass substrate using an oxygen plasma machine to obtain the microchannel chip.

Experiment Example

The experiment example in the present invention is to isolate the circulating tumor cells from the blood. For catching and isolating the CTCs in the blood, the antibody of epithelial cell adhesion molecule (EpCAM) is coated on the surface of the bead.

The Research of the Circulating Tumor Cell (CTC) Caught by Large Beads

1. The Recovery Efficiency and Detection Limit of the Large Beads (200 μm Diameter) in a Non-Microchannel System 10, 1,000 and 100,000 CTCs were respectively put into centrifuge tubes having 1 mL saline buffer (simulation of blood environment) and beads. After thoroughly mixing the CTCs and the beads in the saline buffer, the recovery rate of the beads was observed. Please refer to FIG. 9, the experiment result shows that only 100,000 CTCs' group and 1.5% (about 1500 CTCs) thereof are caught by the beads. However, the large beads did not catch any CTC in 10 CTCs' group and 1000 CTCs' group. The result demonstrates that the large beads cannot catch any CTC when the CTC is less than 1000 in the blood.

2. The Recovery Efficiency and Detection Limit of the Large Beads (200 μm Diameter) in the Microchannel Chip of the Present Invention.

Figure 9:
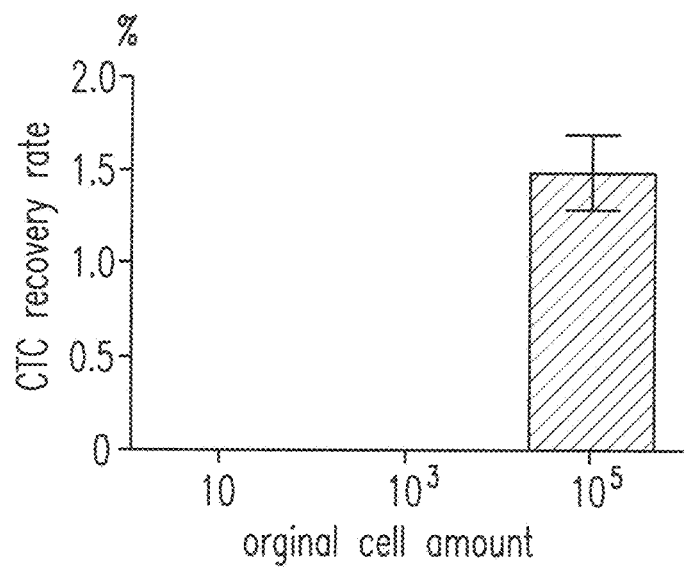
FIG. 9 shows a diagram of the result of the recovery rate and the detection limit without microfluidic system.
Figure 10:
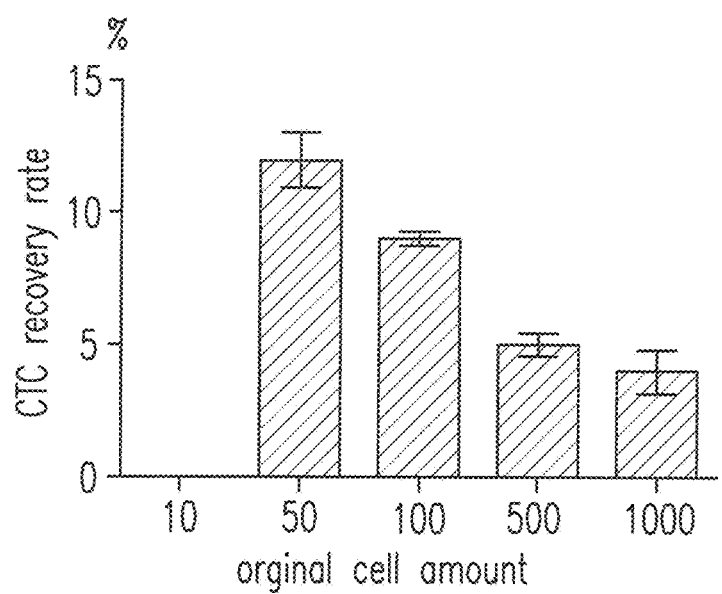
FIG. 10 shows a diagram the result of the recovery rate and the detection limit using the microchannel chip of the present invention.

10, 50, 100, 500 and 1000 CTCs were respectively put into centrifuge tubes having 1 mL saline buffer and beads. After thoroughly mixing the CTCs and the beads in the saline buffer, the mixed solution sample was passed through the microchannel chip of the present invention, and the recovery rate of the beads was observed. Please refer to FIG. 10, the experiment result shows that only 10 CTCs' group were not observed to have any CTC caught by the beads. That is to say, the microchannel chip with the large beads in the present invention can work when the CTCs are more than 50 in the blood. Compared with the result of the non-microchannel system (needs 100,000 CTCs as shown in FIG. 9), the detection limit of the microchannel chip of the present invention is significantly reduced by 2,000 times. Specifically, the sensitivity of the microchannel chip of the present invention is 2,000 times higher than the non-microchannel system. The recovery rate of the microchannel chip of the present invention is on average higher than 5%, which is about 3 times higher than that of the non-microchannel system.

When the average number of CTCs in the blood of the human body is more than 50 per 10 mL, the risk of cancer is very high. Therefore, this experiment demonstrates that the non-microchannel system with large beads (200 μm diameter) cannot determine the risk of cancer. However, the microchannel chip with large beads of the present invention can efficiently and accurately catch CTCs in blood, so as to determine the risk of cancer faster.

Figure 11A:
Figure 11B:
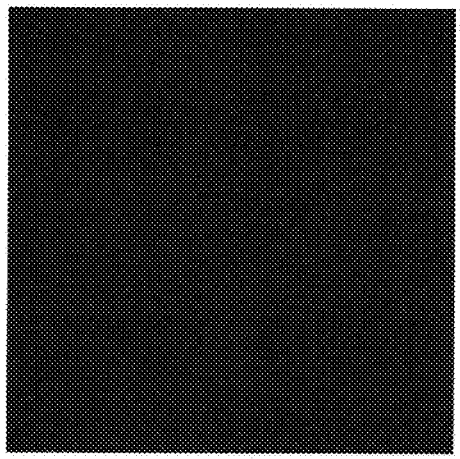
Figure 11C:
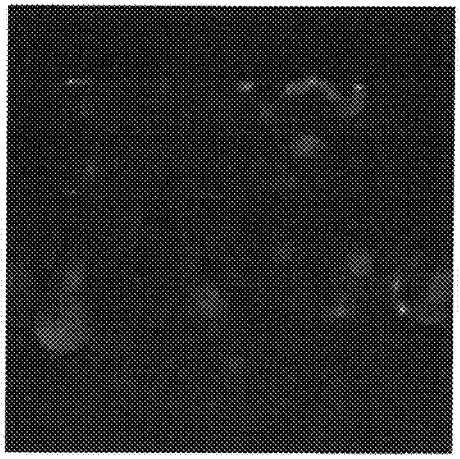

Please refer to FIGS. 11(A)~11(C), which shows the isolation result of a blood specimen flowing through the microchannel chip of the present invention. The blood specimen was obtained from a cancer patient and stained to make CTCs and white blood cells fluoresce, wherein the green fluorescence is CTC, and the red fluorescence is white blood cell. FIG. 11(A) shows CTCs (the green fluorescence) were caught by the beads in the microchannel chip, FIG.

11(B) shows white blood cells (the red fluorescence) were erroneously caught by the beads in the microchannel chip, and FIG. 11(C) shows the sites of all cells caught by the beads by combining FIGS. 11(A) and 11(B). According to FIGS. 11(A)~11(C), this experiment demonstrates that 13 CTCs were caught by the beads in the microchannel chip, and only 3 white blood cells were caught by the beads in the microchannel chip. There are about $10^6$~$10^7$ white blood cells in 1 mL blood of human body. That is to say, only 3 white blood cells were erroneously caught by the bead from million white cells. However, 3000~4000 white blood cells were erroneously caught by a CellSearch system, which is approved by the FDA, from a million white blood cells. Specifically, the erroneous catch rate of the microchannel chip is far lower than that of the CellSearch system. Furthermore, it only needs 30 minutes in this experiment from obtaining the blood specimen to obtaining the image result, which is also far shorter than the prior technique that needs 6~9 hours from pretreatment to obtaining the image result. Therefore, the microchannel chip of the present invention can catch a trace of CTCs in blood effectively, has a low erroneous catch rate, and only takes 30 minutes to obtain the result. Accordingly, the microchannel chip of the present invention can be used as a rapid test biochip for the preliminary detection of cancer.

EMBODIMENTS

1. A microchannel chip loaded with a bead having a particle size, including: a substrate; a body having a first surface, and a second surface covering the substrate; and a patterned structure formed on the second surface to form a microchannel between the body and the substrate, wherein the microchannel includes: a sample entrance extended from the first surface to the second surface, wherein the sample entrance has a diameter to pass a sample therethrough; an expanding section communicating with the sample entrance, wherein the expanding section has a first width; a resistance-increasing section communicating with the expanding section, wherein the resistance-increasing section has a second width; a detecting section communicating with the resistance-increasing section, wherein the bead is configured in the detecting section; and a slow flow section communicating with the detecting section, and having a first depth, wherein the particle size is larger than the first depth to prevent the bead from entering the slow flow section, the second width is smaller than either of the first width and the diameter, and the bead is moored in the detecting section.

2. The microchannel chip according to Embodiment 1, wherein the detecting section comprises a main detecting section having a first side wall, a second side wall and an upper wall, and at least one of the first side wall, the second side wall and the upper wall has an uneven structure to confront a flow direction of the sample to increase a contact chance of the sample with the bead.

3. The microchannel chip according to Embodiment 1 or 2, wherein the uneven structure is at least one of a comb structure, a wave structure, a sawtooth structure and a semi-circular protrusion structure.

4. The microchannel chip according to any one of Embodiments 1 to 3, wherein the expanding section comprises a first end and a second end, the first end communicates with the sample entrance, the second end communicates with the resistance-increasing section, and the first width is gradually narrowed to the second width at the second end of the expanding section.

5. The microchannel chip according to any one of Embodiments 1 to 4, wherein the first surface is opposite to the second surface, and the detecting section has a second depth to moor therein only a single respective bead at a specific point thereof.

6. The microchannel chip according to any one of Embodiments 1 to 5, wherein the substrate includes a material being polymethylmethacrylate (PMMA), polyethylene terephthalate (PET), polycarbonate (PC), polydimethylsilicon (PDMS), silica gel, rubber, plastic or glass, and the body includes a material being polymethylmethacrylate (PMMA), polyethylene terephthalate (PET), polycarbonate (PC), polydimethylsilicon (PDMS), silica gel, rubber or plastic.

7. The microchannel chip according to any one of Embodiments 1 to 6, wherein the sample is a body fluid or a bacterial solution.

8. A microchannel structure loaded with a bead having a particle size, including a structure body for passing a sample through the microchannel structure to have a test or a treatment, wherein the structure body includes: a sample entrance having a first aperture to allow the sample passing therethrough; a resistance-increasing section connected with the sample entrance, and having a second aperture being smaller than the first aperture; a detecting section having a first end and a second end for testing or treating the sample, wherein the first end connects with the resistance-increasing section; and a bead mooring structure coupled to the second end for mooring the bead in the detecting section.

9. The microchannel structure according to Embodiment 8, wherein the detecting section further includes a main detecting section having a peripheral wall, and at least a portion of the peripheral wall has an uneven structure to confront a flow of the sample to increase a contact chance of the sample with the bead.

10. The microchannel structure according to Embodiment 8 or 9, wherein the confrontation by the uneven structure increases a turbulence level of the flow.

11. The microchannel structure according to any one of Embodiments 8 to 10, wherein the uneven structure is at least one of a comb structure, a wave structure, a sawtooth structure and a semi-circular protrusion structure.

12. The microchannel structure according to any one of Embodiments 8 to 11, further including a slow flow section connected with the second end of the detecting section, wherein the slow flow section has a third aperture, and the second end of the detecting section has a fourth aperture.

13. The microchannel structure according to any one of Embodiments 8 to 12, wherein the bead mooring structure is the second end of the detecting section or the slow flow section.

14. The microchannel structure according to any one of Embodiments 8 to 13, wherein when the bead mooring structure is the second end of the detecting section, the third aperture is smaller than the particle size, and when the bead mooring structure is the slow flow section, the fourth aperture is smaller than the particle size such that the bead is moored in the detecting section.

15. The microchannel structure according to any one of Embodiments 8 to 14, wherein the third aperture has a width the same as that of the fourth aperture.

16. The microchannel structure according to any one of Embodiments 8 to 15, wherein the sample is a body fluid or a bacterial solution.

17. A method for detecting whether a biological substance exists in a sample using a microchannel structure, including: providing a microchannel structure including a plurality of beads moored therein, wherein a plurality of catchers are coated on a surface of each of the plurality of beads, and the plurality of catchers catch the biological substance in the sample; obtaining the sample; and causing the sample to flow through the microchannel structure so as to confirm whether the biological substance exists in the sample.

18. The method according to Embodiment 17, further including a step of: analyzing the biological substance caught by the plurality of catchers.

19. The method according to Embodiment 17 or 18, wherein the sample is a body fluid or a bacterial solution, and the biological substance includes one selected from a group consisting of a circulating tumor cell (CTC), a circulating stem cell (CSC), a fetal cell, a bacteria, a virus, an epithelial cell and an endothelial cell.

20. The method according to any one of Embodiments 17 to 19, wherein the sample is a blood, the biological substance is a circulating tumor cell (CTC), and the catcher is an antibody of an epithelial cell adhesion molecule (EpCAM).

In summary, the present invention provides a new concept that the microchannel chip with large beads can effectively catch the trace CTCs in blood, and the erroneous catch rate of the microchannel chip is very low, so that the microchannel chip can determine the risk of cancer early. Furthermore, the microchannel chip of the present invention only needs 20~30 large beads, which can significantly reduce manufacturing costs.

Although the present invention has been described with reference to certain exemplary embodiments thereof, it can be understood by those skilled in the art that a variety of modifications and variations may be made to the present invention without departing from the spirit or scope of the present invention defined in the appended claims, and their equivalents.

What is claimed is:

1. A microchannel structure loaded with a bead having a particle size, comprising a structure body for passing a sample through the microchannel structure to have a test or a treatment, wherein the structure body comprises:
    a sample entrance having a first aperture to allow the sample passing therethrough;
    a resistance-increasing section connected with the sample entrance, and having a second aperture being smaller than the first aperture;
    a detecting section having a first end and a second end for testing or treating the sample, wherein the first end connects with the resistance-increasing section;
    slow flow section connected with the second end of the detecting section, wherein the slow flow section has a third aperture, and the second end of the detecting section has a fourth aperture; and
    a bead mooring structure coupled to the second end for mooring the bead in the detecting section, wherein when the bead mooring structure is the second end of the detecting section, the third aperture is smaller than the particle size, and when the bead mooring structure is the slow flow section, the fourth aperture is smaller than the particle size such that the bead is moored in the detecting section.

2. The microchannel structure as claimed in claim 1, wherein the detecting section further includes a main detecting section having a peripheral wall, and at least a portion of the peripheral wall has an uneven structure to confront a flow of the sample to increase a contact chance of the sample with the bead.

3. The microchannel structure as claimed in claim 2, wherein the confrontation by the uneven structure increases a turbulence level of the flow.

4. The microchannel structure as claimed in claim 2, wherein the uneven structure is at least one of a comb structure, a wave structure, a sawtooth structure and a semi-circular protrusion structure.

5. The microchannel structure as claimed in claim 1, wherein the third aperture has a width the same as that of the fourth aperture.

6. The microchannel structure as claimed in claim 1, wherein the sample is a body fluid or a bacterial solution.

7. A method for detecting whether a biological substance exists in a sample using a microchannel structure as claimed in claim 1, comprising:
    providing a microchannel structure including a plurality of beads moored therein, wherein a plurality of catchers are coated on a surface of each of the plurality of beads, and the plurality of catchers catch the biological substance in the sample;
    obtaining the sample; and
    causing the sample to flow through the microchannel structure so as to confirm whether the biological substance exists in the sample.

8. The method as claimed in claim 7, further comprising a step of:
    analyzing the biological substance caught by the plurality of catchers.

9. The method as claimed in claim 7, wherein the sample is a body fluid or a bacterial solution, and the biological substance includes one selected from a group consisting of a circulating tumor cell (CTC), a circulating stem cell (CSC), a fetal cell, a bacteria, a virus, an epithelial cell and an endothelial cell.

10. The method as claimed in claim 7, wherein the sample is a blood, the biological substance is a circulating tumor cell (CTC), and the catcher is an antibody of an epithelial cell adhesion molecule (EpCAM).

* * * * *